United States Patent [19]
Trabucco

[11] 3,978,865
[45] Sept. 7, 1976

[54] IMPLANTABLE PACEMAKER AND ELECTRODE MEMBER THEREFOR

[76] Inventor: Hector Osvaldo Trabucco, Av.Santa Fe 2926, VI°B, Buenos Aires, Argentina

[22] Filed: Jan. 22, 1975

[21] Appl. No.: 542,944

[30] Foreign Application Priority Data
Jan. 25, 1974 Argentina .......................... 252075

[52] U.S. Cl. ............................. 128/419 P; 128/418
[51] Int. Cl.² ........................................... A61N 1/36
[58] Field of Search ............... 128/404, 418, 419 R, 128/419 P, 421, 422, 423, 419 PG

[56] References Cited
UNITED STATES PATENTS

| | | | |
|---|---|---|---|
| 3,253,595 | 5/1968 | Murphy, Jr. et al. | 128/418 |
| 3,814,104 | 6/1974 | Irnich et al. | 128/418 |
| 3,880,169 | 4/1975 | Starr et al. | 128/418 |

Primary Examiner—William E. Kamm
Attorney, Agent, or Firm—Karl F. Ross; Herbert Dubno

[57] ABSTRACT

An electrode member insertable from without through the epicardium into the heart muscle, as part of an implantable pacemaker, comprises a holder of dielectric elastic material including a tubular stem terminating in an enlarged resilient pad having the shape of a platform. One major surface of the platform pivotally supports a metallic hook which is swivelable about an axis perpendicular to that surface and is electrically connected to a conductor extending within the stem to a generator of electric pulses. Upon insertion of the hook from the outside through the epicardium into the heart muscle by a tool gripping that hook, release of the hook allows the elastic pad to expand against the outer heart surface to anchor the electrode member in position.

16 Claims, 8 Drawing Figures

U.S. Patent  Sept. 7, 1976  3,978,865
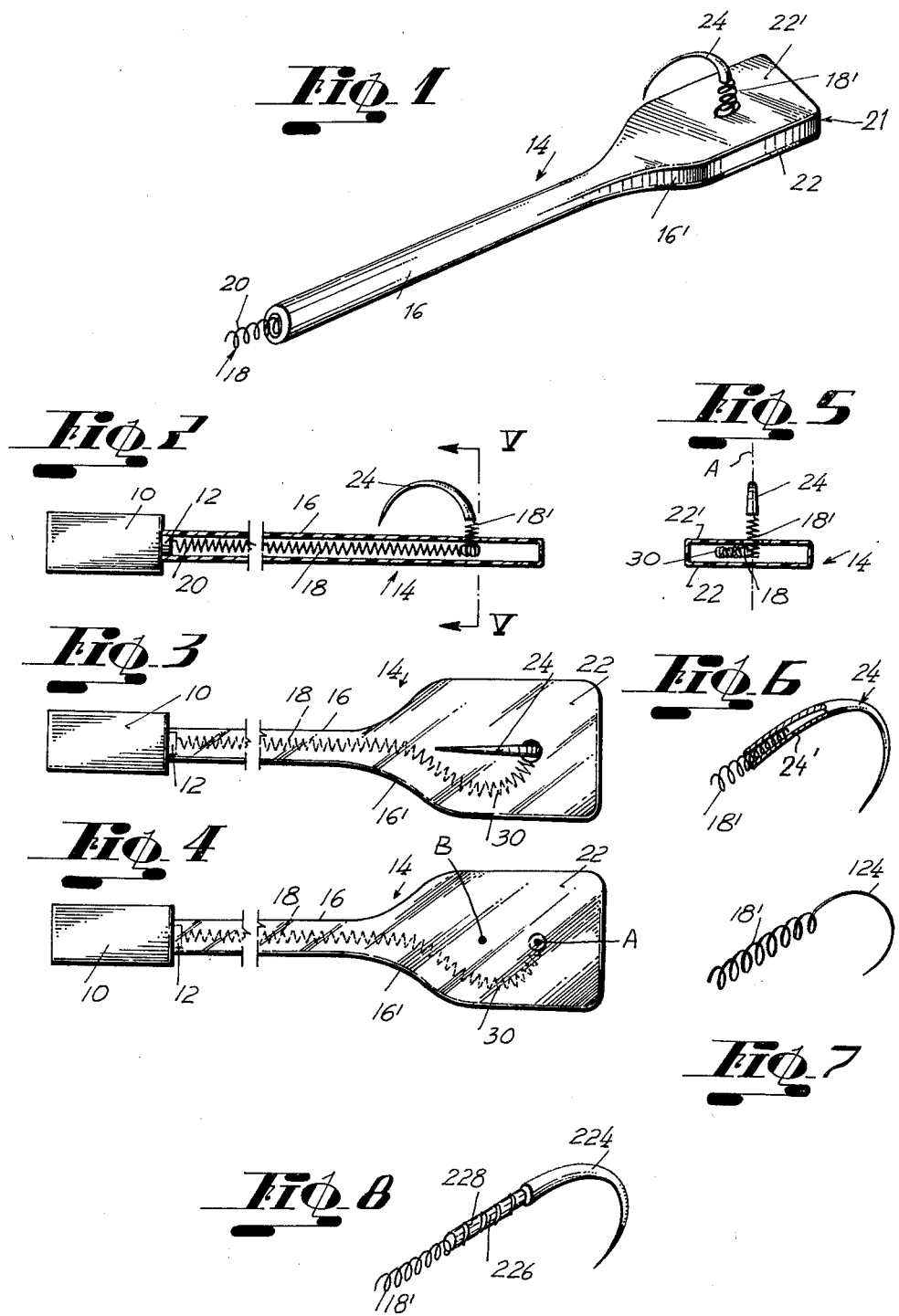

IMPLANTABLE PACEMAKER AND ELECTRODE MEMBER THEREFOR

Field of the Invention

My present invention relates to an implantable pacemaker and to a catheter-type electrode member insertable from the outside through the epicardium into the heart muscle, as part of such a pacemaker, for conveying electric stimuli of the epicardiac or the intramyocardiac type upon energization by an electric pulse generator.

BACKGROUND OF THE INVENTION

A conventional catheter-type electrode member, to be used as part of a cardiac pacemaker, includes an insulated conductor whose dielectric sheath terminates in a flat platform-shaped pad, the conductor having a straight tip projecting from that pad for insertin into the heart muscle which for this purpose must be perforated beforehand. To maintain this projecting tip within the perforation in the heart muscle, it is necessary to suture the platform to the heart muscle after insertion in order to prevent any dislodgment of the tip by the movement of the heart muscle.

With a view to more firmly anchoring the conductor tip to the heart muscle, it has been proposed to give it the shape of a helix. This has the drawback that its insertion in the heart muscle requires the preliminary drilling of a rather large hole therein. It is furthermore extremely difficult to predetermine the correct length of the conductor tip to be inserted, in order to keep it from penetrating the ventricular chamber. Moreover, the conductor has a tendency to break at the point where the helix enters the heart. Finally, the surgeon has to prepare at the start of the operation a rather substantial access opening in the thorax enabling the helix to be threaded into the muscle by rotating it about its axis. For proper penetration that axis must be substantially perpendicular to a plane tangent to the heart-muscle surface at the point of insertion, this condition greatly complicating the task of the operator.

OBJECTS OF THE INVENTION

The general object of my present invention, therefore, is to provide an improved implement of the character described which obviates the aforedescribed disadvantages and can be implanted in a simple manner.

A more particular object is to provide means in such an implement for clamping an implanted conductor extremity to the heart muscle without additional surgical intervention.

SUMMARY OF THE INVENTION

In accordance with the present invention I provide a catheter-type electrode member for an implantable pacemaker, insertable from without through the epicardium into the heart muscle for the purpose of cardiac stimulation, which comprises a holder of dielectric material including a stem and an enlarged elastic pad. The holder encloses conductor means, specifically a single wire, connectable to an external source of electric pulses, the conductor means extending through the stem into the pad and forming therein a helically coiled portion which projects outwardly from a substantially flat major pad surface and terminates therebeyond in an arcuately curved electrically conductive hook of generally semicircular shape lying in a plane substantially perpendicular to the pad surface; a tip of the hook, pointing back toward this major pad surface, serves to hold the pad in a sutureless manner onto the surface of a patient's heart upon penetrating the epicardium.

Pursuant to another aspect of my invention there is provided an implantable pacemaker including the aforedescribed electrode member together with a generator of electric pulses connected to its conductor means.

In use, the surgeon implants the hook through the epicardium in the patient's heart muscle with the aid of a tool gripping that hook while the heart muscle represses the resilient pad. As soon as that hook is released, the pad re-expands and gently but firmly clamps the hook under this resilient pressure to the muscle to prevent its spontaneous detachment therefrom. The approximately semicircular shape of the hook is particularly advantageous since it lets the tip of the hook come to rest against the pad upon reiease of the former, thereby positively shackling the holder to the flesh. Removal of the hook, however, is equally simple by the use of a similar tool and recompression of the pad to facilitate unhooking.

In a preferred embodiment, the stem is tubular and merges integrally into the resilient pad, the latter having the shape of a platform whose thickness substantially equals the outer diameter of the stem; this provides a highly compact structure occupying a minimum of space within the patient's chest.

According to another advantageous feature of my invention, the conductor extending within the holder is a helically coiled wire portion which is curved inside the pad about a line perpendicular to the aformentioned major pad surface; this axis is in line with an extremity of the wire is integral or otherwise rigidly connected with the hook which is swivelable about an axis parallel to that line.

The insertion is carried out by exerting pressure on the pointed end of the hook but not necessarily in a direction perpendicular to the outer surface of the heart. Thus, the surgeon may first explore the heart in the patient's body to find a proper access spot (without fat) and then insert the sharpened end from any convenient angle. The access opening can therefore be much smaller than with the conventional implements described above.

BRIEF DESCRIPTION OF THE DRAWING

The above and other features of my invention will now be described in detail with reference to the accompanying drawing in which:

FIG. 1 is a perspective view of an electrode member according to my invention;

FIG. 2 is a longitudinal sectional view of the electrode member of FIG. 1;

FIG. 3 is a top plan view of the member shown in FIGS. 1 and 2;

FIG. 4 is a bottom plan view of the same member;

FIG. 5 is a cross-sectional view taken on the line V—V of FIG. 2;

FIG. 6 is a perspective detail view; and

FIGS. 7 and 8 are views similar to FIG. 6, showing two modifications.

SPECIFIC DESCRIPTION

In FIGS. 1–4 I have shown an electrode member 14 for an implantable pacemaker also including an electric generator 10, illustrated schematically in FIGS. 2–4, of a construction well known per se.

According to my present invention, the electrode member 14 comprises a resilient, preferably transparent tubular stem 16 of dielectric material, e.g. a synthetic elastomer, which surrounds a flexible electrical conductor 18 whose left-hand end 20 engages a supply terminal 12 in the output of generator 10. The conductor 18 is a helical wire having a high degree of flexibility. The stem 16 integrally terminates at its forward, right-hand end 16' in a flat, resilient, preferably also transparent pad 21 in the shape of a platform with two parallel major surfaces 22, 22' whose spacing, in its normal compressed state, equals the inner diameter of stem 18 so that the thickness of the pad corresponds to the outer stem diameter. The right-hand extremity 18' is a helically wound conductor portion which of wire 18 projects perpendicularly outwardly, along an axis A, through the surface 22' of the otherwise imperforate pad 21. The portion of wire coil 18 which is received within the pad 21 — merging into extremity 18' at axis A — follows a soft curve 30 approximately centered on a line B parallel to axis A.

Accordiing to FIGS. 1–6, extremity 18' projecting from pad surface 22' is rigid with a sharp-pointed hook 24 swivelable about axis A; hook 24 extends along a nearly semicircular arc in a plane including this axis, its pointed end being biased rearwardly so as normally to face the stem 16.

As best seen in FIG. 6, the hook 24 has a hollow shank 24' into which the wire extremity 18' is press-fitted.

According to a modification shown in FIG. 7, the conductor extremity 18' is integrally extended to form a hook 124 of the shape described above.

In FIG. 8 I have shown a hook 224 similar to hook 24 having a reduced shank 226, provided with a helical groove 228, into which the coil exremity 18' is threaded so as to embrace that shank without increasing its effective thickness.

In all embodiments the pointed end of the hook is preferably solid.

The resiliency of pad 21 enables the surgeon to grip the hook 24, 124 or 224 with the aid of a suitable tool and, by applying the requisite pressure, to insert it into the heart muscle. The swivelable coil extremity 18' provides the necessary freedom of movement for the hook as the pad resiliently yields during this operation. As soon as the surgeon withdraws the gripping tool, the pad regains its original shape and abuts against the outer surface of the heart i.e. the epicardium, thereby firmly anchoring the hook in the flesh.

It will thus be seen that no special suturing step is required for attaching the pad to the heart. The resiliency of the pad maintains its contact with the epicardial surface in spite of the ongoing heartbeat and thus prevents the hook from detaching itself, thereby insuring continuity of electrical stimulation of the heart by the electrical pulses.

The overall length of electrode 14 may be up to about 140 cm, preferably 105 cm. The height of the vertex of hook 24, 124 or 224 above pad surface 22' may vary from a few millimeters to about 5 cm. A pad surface of about 16 cm² has been found highly suitable.

I claim:

1. A catheter-type electrode member for an implantable pacemaker, insertable from without through the epicardium into the heart muscle for cardiac stimulation, comprising:
    a holder of dielectric material including a stem and an enlarged elastic pad having a substantially flat major surface; and
    conductor means connectable to an external source of electric pulses, said conductor means extending through said stem into said pad and forming therein a helically coiled portion projecting outwardly from said major surface, said portion terminating therebeyond in an arcuately curved electrically conductive hook of generally semicircular shape lying in a plane substantially perpendicular to said major surface and having a tip pointing back toward said major surface for holding said pad in a sutureless manner onto the heart surface upon penetrating the epicardium, with exertion of resilient pressure by said pad upon the heart.

2. An electrode member as defined in claim 1 wherein said stem is tubular and merges integrally into said pad.

3. An electrode member as defined in claim 2 wherein said pad is platform-shaped and has a thickness substantially equaling the outer diameter of said stem.

4. An electrode member as defined in claim 1 wherein said conductor means comprises a single wire.

5. An electrode member as defined in claim 4 wherein said helically coiled portion is curved in said pad about a line perpendicular to said major surface and has an extremity on an axis parallel to said line, said hook being rigid with said extremity and swivelable about said axis.

6. An electrode member as defined in claim 5 wherein said hook is integral with said wire.

7. An electrode member as defined in claim 5 wherein said hook has a hollow shank receiving said extremity with a frictional fit.

8. An electrode member as defined in claim 5 wherein said hook has a shank embraced by terminal turns of said helically coiled portion.

9. In an implantable pacemaker for cardiac stimulation, in combination, a generator of electric pulses and a catheter-type electrode insertable from without through the epicardium into the heart muscle for cardiac stimulation, said electrode comprising:
    a holder of dielectric material including a stem and an enlarged elastic pad having a substantially flat major surface; and
    conductor means connectable to said generator, said conductor means extending through said stem into said pad and forming therein a helically coiled portion projecting outwardly from said major surface, said portion terminating beyond said major surface in an arcuately curved electrically conductive hook of generally semicircular shape lying in a plane substantially perpendicular to said major surface and having a tip pointing back toward said major surface for holding said pad in a sutureless manner onto the heart surface by said pad upon the heart.

10. The combination defined in claim 9 wherein said stem is tubular and merges integrally into said pad.

11. The combination defined in claim 10 wherein the thickness of said pad substantially equals the outer diameter of said stem.

12. The combination defined in claim 9 wherein said conductor means comprises a single wire.

13. The combination defined in claim 12 wherein said helically coiled portion is curved in said pad about a line perpendicular to said major surface and has an extremity on an axis parallel to said line, said hook being rigid with said extremity and swivelable about said axis.

14. The combination defined in claim 13 wherein said hook is integral with said wire.

15. The combination defined in claim 13 wherein said hook has a hollow shank receiving said extremity with a frictional fit.

16. The combination defined in claim 5 wherein said hook has a shank embraced by terminal turns of said helically coiled portion.

* * * * *